United States Patent [19]
Vega

[11] 4,249,536
[45] Feb. 10, 1981

[54] UROLOGICAL CATHETER

[76] Inventor: Roger E. Vega, R.D. #7, Twin Oak, Kittanning, Pa. 16201

[21] Appl. No.: 38,745

[22] Filed: May 14, 1979

[51] Int. Cl.³ .............................................. A61M 25/00
[52] U.S. Cl. ................................................. 128/349 B
[58] Field of Search .............. 128/349 R, 349 B, 348, 128/350 R, 351, 246, 344, 239

[56] References Cited

U.S. PATENT DOCUMENTS

| | | | |
|---|---|---|---|
| 2,936,761 | 5/1960 | Snyder | 128/349 B |
| 3,896,816 | 7/1975 | Mattler | 128/349 B |
| 4,143,651 | 3/1979 | Patel | 128/349 B |
| 4,148,319 | 4/1979 | Kasper et al. | 128/349 B |
| 4,157,094 | 6/1979 | Patel | 128/349 B |

*Primary Examiner*—John D. Yasko
*Attorney, Agent, or Firm*—Thomas H. Murray; Clifford A. Poff

[57] ABSTRACT

A flexible retention catheter includes a soft, pliable cone-shaped tip with a reduced urethral contact surface defined by spiral grooves or hair-like projections. A magneto-insert embedded within the tip is used in cooperation with an electromagnet externally of the catheter to propel the catheter along the urethra by repulsive or attractive lines of magnetic force. In one embodiment, the tip of the catheter is partially divided along one transverse line to form a hinged tip segment and in another embodiment, the tip portion is divided longitudinally along a line intersecting with a transverse dividing line forming two hinged tip segments. The segments are releasably joined by releasable fasteners. The hinged tip segments are swung about the hinge connection against the inflated surface of the balloon by tension strips that extend along the balloon and move in response to a distention thereof to expose the drainage lumen within the tip. Other string actuators also traverse the balloon and elastically spread diametrically-divided end segments of a portion of the lumen to retain a segment of the catheter in situ in the urethra while the remaining portion of the lumen disjoined therefrom is withdrawn from the urethra. The implanted portion of the catheter is adjoined with an inflation lumen that extends along the length of the urethra. A collapsible sheath is adhered to the implanted segment in a fluid-conducting relation with the drainage lumen thereof.

30 Claims, 8 Drawing Figures

UROLOGICAL CATHETER

BACKGROUND OF THE INVENTION

The present invention is addressed to improvements in urological catheters to minimize the possible injury to the urethra and bladder of a patient. More particularly, the present invention provides an improved construction for a urological catheter to minimize frictional contact with the urethra during movement therealong; to enhance the necessary advancing movement of the catheter along the urethra through magnetic means for propelled movement or bestow directionability to the advancing tip and to utilize distention of a retention balloon as an actuator of a mechanism employed to expose the drainage lumen in the catheter and, if desired, operate a retention mechanism for in situ support in the urethra of a segmented portion of the catheter while the disjoined part of the drainage lumen is withdrawn from the urethra.

The Foley catheter is a well-known form of a urological catheter employing a retention balloon that is inflated after insertion into a patient's bladder. The catheter is primarily used to drain the human bladder when there is an obstruction by the prostate gland and other causes, such as after surgery and to treat urinary inconvenience of senility and paralytic conditions of the body. A urological catheter is frequently used during post-surgery recovery, particularly after surgical removal of the prostate to alleviate a blockage in the area of the bladder. The catheter is used in other instances where the need to alleviate a blockage arises, even though the patient's natural sphincter is functionally useful but rendered inoperative due to the presence of a catheter.

Problems and shortcomings arise out of the use of the Foley catheter as presently manufactured. The catheter must be advanced along the human urethra by pushing blindly which sometimes tears the lining of the urethra and causes bleeding, infection and scar formation in the urethra. The catheter typically has drainage eyelets in a blunt, solid tip which presents a relatively large surface area causing adverse frictional contact with the urethra. Such a tip is not hydrodynamically efficient. Near the distal end, the two eyelets in the tip portion of presently-available catheters weaken the tip, permitting it to buckle during movement along the urethra. This buckling is believed to occur because of the aligned arrangement of the eyelets at diametrically-opposite sites which brings about a dramatic symmetrical weakening to the side wall of the tip. When the tip buckles, protruding edges develop, particularly at the sites of the eyelets causing a scratching of the lining of the urethra which, in turn, produces bleeding and injury. The cuff or retention balloon of the catheter is not biogenetically shaped to conform to the shape of the bladder neck. After distention of the balloon, the tip of the catheter protrudes therefrom to an excessively large distance such that injury to the bladder wall is possible as the wall of the bladder contacts the protruding tip. Moreover, the drainage eyelet openings in the tip of the catheter are spaced from the wall of the inflated retention balloon, thus causing an obstruction preventing complete drainage of the bladder.

SUMMARY OF THE INVENTION

It is an object of the present invention to provide improvements to a retention catheter for more efficient and directional insertion with reduced friction while moving along the urethra to eliminate or at least minimize any damage to the lining of the urethra.

It is a further object of the present invention to provide an improved retention catheter wherein distention of a retention balloon is utilized to form an actuator for exposing the entire cross-sectional area of the drainage lumen in the catheter and/or provide retention for a segmental part of the catheter while located within the urethra.

More particularly, according to the present invention there is provided a flexible retention catheter including a soft, pliable cone-shaped tip on the end of an elongated tubular body portion defining a drainage lumen and in association therewith is an inflation lumen extending into communication with an inflatable balloon forming a sheath around the body portion adjacent the tip, the tip having a reduced urethral contact surface defined by recesses for minimizing sliding friction during travel of the tip along the lining of a human urethra, the tip having a side wall defining a drainage eyelet extending into communication with a drainage lumen within the tip. In one form, the urethral contact surface of the tip is defined by spiral grooves extending along the tip from the closed end thereof. In another form, the urethral contact surface of the tip is defined by hair-like projections. The tip is preferably a discrete member adhered by radio-frequency welding or other measures to the distal end of the body portion for guiding and flexible movement along the urethra, particularly in regard to providing conforming flexibility to the curves of the human male urethra. Conforming flexibility is also obtained according to a particularly unique aspect of the present invention wherein the tip is partly divided along a transverse line or attached to the main shaft of the catheter by a hinge joint. This bestows directional flexing to the tip so that it pivots about the hinge to follow the concave curvature of the male urethra.

The retention catheter of the present invention is particularly characterized by the employment of magnetic means including a magnetoinsert supported by a tubular body portion of the catheter preferably by embedded support within the wall of a catheter tip for propelled movement of the body portion of the catheter along the urethra. The magnetic means preferably further includes means external of the tubular body portion of catheter for establishing a force field effective in cooperation with the force field of the magnetoinsert to direct and guide the tip of the catheter along the urethra. The force field thus established for propelled movement of the tubular body portion of the catheter is either magnetically repulsive or attractive in a dependent relation upon the site of the magnetic means which is external of the catheter.

The present invention further provides a retention catheter wherein a soft, pliable one-shaped tip portion on the end of the tubular body portion is disposed adjacent a distensible retention balloon, a drainage lumen in the body portion communicating with a drainage lumen in the tip defined by side walls which are severed along at least one line to form a hinged tip segment, at least one tension member traversing the balloon and adhered at one end to the hinged tip segment and adhered to the other end of the body portion of the catheter at the side of the balloon which is remote to the tip segment, and in inflation lumen disposed in association with the body portion of the catheter extending into communication with the balloon for conducting an inflating medium to the balloon whereby inflation thereof moves the tensioning member to swing the hinged tip segment against the inflated surface of the balloon for exposing the cross-sectional area of the drainage lumen in the tip portion of the catheter. It is preferred to provide that the inflatable balloon is constructed and attached to the body portion of the catheter so that upon distention of the balloon, the surface thereof extends toward the tip portion for a deformed nested support of the hinged tip segment upon displacement thereof. A single dividing line is sufficient to provide the hinged tip segment. In a second embodiment, two hinged tip segments are formed by one dividing line extending parallel to the extended length of the catheter to intersect with a dividing line at right angles thereto forming the two hinged tip segments each coupled to a tension member for actuation upon distention of the inflatable balloon. Each such hinged tip segment is displaced to expose the entire area of the drainage lumen of the catheter.

Distention of the inflatable balloon is employed in a further aspect of the present invention to detach an adjoined carrier portion from an implantable catheter portion. The implantable catheter portion is a relatively short segment of a tubular body portion having a proximal end with a divided side wall along a plane parallel to the drainage lumen therein. The segments formed by the divided side wall are connected by tensioning members for outward movement against the wall of the urethra upon distention of the inflatable balloon. The arrangement of parts is such that the catheter has an implantable end portion which is detachable, upon distention of the inflatable balloon, for retention in the urethra by elastic movement of the catheter wall segments against the wall of the urethra and at a distally-spaced site by distention of the inflatable balloon. After disjoining of the implantable segment from the remaining portion of the catheter, the latter is withdrawn from the urethra leaving the implanted portion anchored at the desired site with only a relatively small inflation lumen extending along the urethra from the body of a patient. If it is desired, a thin, pliable sheathing of plastic material extends from the implanted portion of the catheter through the remaining length of the urethra and from the body of a patient.

These features and advantages of the present invention as well as others will be more fully understood when the following description is read in light of the accompanying drawings, in which:

Figures 1, 2, 8:
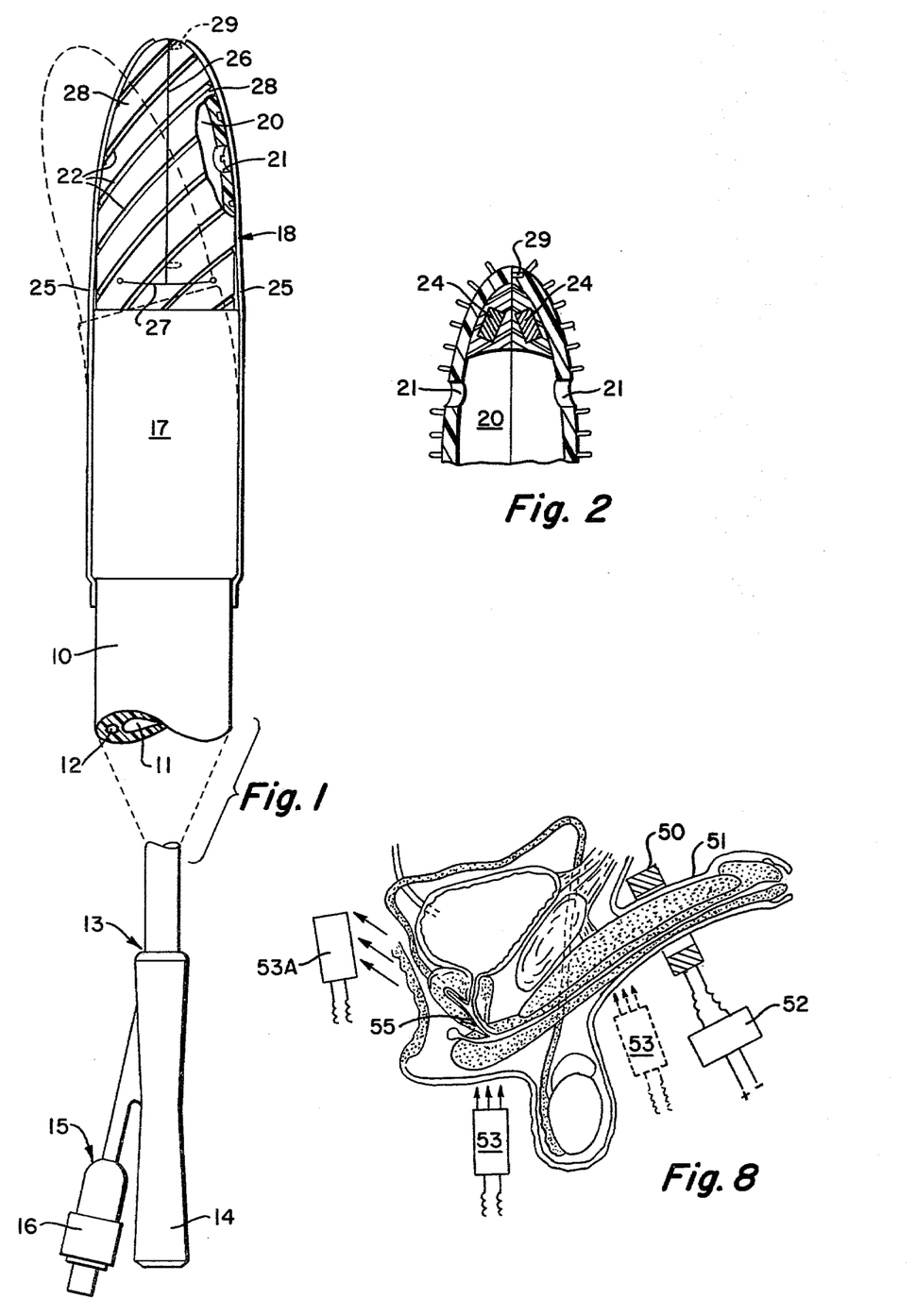
FIG. 1 is an enlarged view, partly in section, of a catheter embodying a soft, pliable tip with friction-reducing surfaces according to one embodiment of the present invention.
FIG. 2 is an enlarged view similar to a portion of FIG. 1 showing a second embodiment of the friction-reducing surfaces on the tip of the catheter.
FIG. 8 illustrates the arrangement of parts to utilize lines of magnetically-attractive and repulsive forces to propel a catheter along a human male urethra.

According to the embodiment of the present invention shown in FIG. 1, there is provided a urological catheter including a tubular body portion 10 having side walls defining a drainage lumen 11. The tubular body portion 10 is made from polyvinylchloride with a sufficient plasticizer for moderate deformation under a relatively small force while essentially maintaining the integrity of the drainage lumen. Other materials, such as latex and silicon rubber, may be used to form the body portion 10. An inflation lumen 12 is defined in the side wall of the tubular body portion or otherwise disposed in association with the tubular body portion to extend substantially along the entire length thereof. At one end of the tubular body portion 10 there is provided a proximal assembly 13 including a socket connector 14 used to couple the drainage lumen to a drainage tube or other implement. The proximal assembly 13 further includes an inflation plug assembly 15 communicating with valve means 16. The valve means includes a socket connector for coupling to a conventional inflation member such as a syringe used to introduce and withdraw an inflating medium through the valve means, plug 15 and inflation lumen 12. The proximal assembly is shown at a reduced size as compared with the illustration of the distal end portion of the catheter.

An inflatable balloon 17 is sheathed around the distal end of the catheter at a spaced location from a conical tip 18. The balloon is adhered to the outer side wall surfaces of the tubular body portion forming an airtight compartment therebetween with which there communicates an inflation channel 19 (FIG. 3) extending through the side wall of the body portion into communication with the inflation lumen 12. The inflatable balloon is constructed from latex or other soft rubber-like material and adhered to the tubular body portion in a manner to envelop a greater portion of the tubular body portion by distention toward the tip 18 and toward the proximal assembly. The purpose of such distention of the inflatable balloon will be described in greater detail hereinafter. The tip 18 is preferably constructed as a unitary member and connected to the tubular body portion by radio-frequency welding or by other means well known in the art, such as adhesives, mechanical interconnections, heat welding, etc. The tip 18 may also be made of the same material as the main body of the catheter.

The tip 18 embodies the shape of a truncated cone and made from soft, pliable material such as plasticized polyvinylchloride to provide a softness and pliable to a far greater extent than the tubular body portion 10. Latex and silicon rubber materials may be used to form the tip 18. The tip has a cone-shaped configuration for hydrodynamically and tissue dynamically be efficient to move along the urethra without injury thereto. Moreover, the tip is sufficiently pliable and flexible to conform to curves encountered during passage along the human male urethra. Flexibility for this same purpose is also achieved by a hinged area of attachment of the tip or a segment thereof to the body portion. While the tip is preferably constructed from polyvinylchloride with a sufficient plasticizer to achieve the desired softness and pliability, the tubular body portion 10 is also constructed, if desired, of polyvinylchloride using less plasticizer to prevent unwanted collapse of the side walls that might otherwise produce a blockage to the drainage lumen 11 and/or inflation lumen 12.

As shown in FIG. 1, the tip is formed by a wall section enclosing a drainage lumen 20 communicating with the drainage lumen 11 in the tubular body portion. Drainage eyelets 21 extend in the side wall of the tip to drainage lumen 20. The external surface area of the tip which would normally contact the urethra is reduced so as to surface area by spirally-shaped grooves 22 in accordance with the embodiment of the invention shown in FIG. 1. The grooves 22 are employed to reduce frictional contact of the tip with the urethra during advancing movement therealong.

A further embodiment of a reduced urethral contact surface is shown in FIG. 2 wherein short hair-like projections 23 extend from the outer surface of the tip for even greater reduced frictional contact with the urethra. The projections 23 are preferably molded as an integral part of the tip and produced with a softness and flexibility to avoid any possibility of scratching or tearing of the lining of the urethra. The projections yield under very nominal forces while maintaining a very small contact area with the lining of the urethra at an almost absolute nominal minimum. FIG. 2 illustrates a still further aspect of the present invention wherein magnetic means are utilized for developing a propelling force upon the catheter for movement along the urethra. In this aspect of the invention, one or magnetic inserts 24 are embedded within filler material occupying an unused distal tip portion of the drainage lumen. If desired, the inserts may be anchored within the side wall of the tip or even embedded within the tubular body portion 10 without departing from the spirit of the present invention. The mode of use for the magnetic inserts will be described in greater detail hereinafter in regard to the illustration by FIG. 8.

Figure 3:
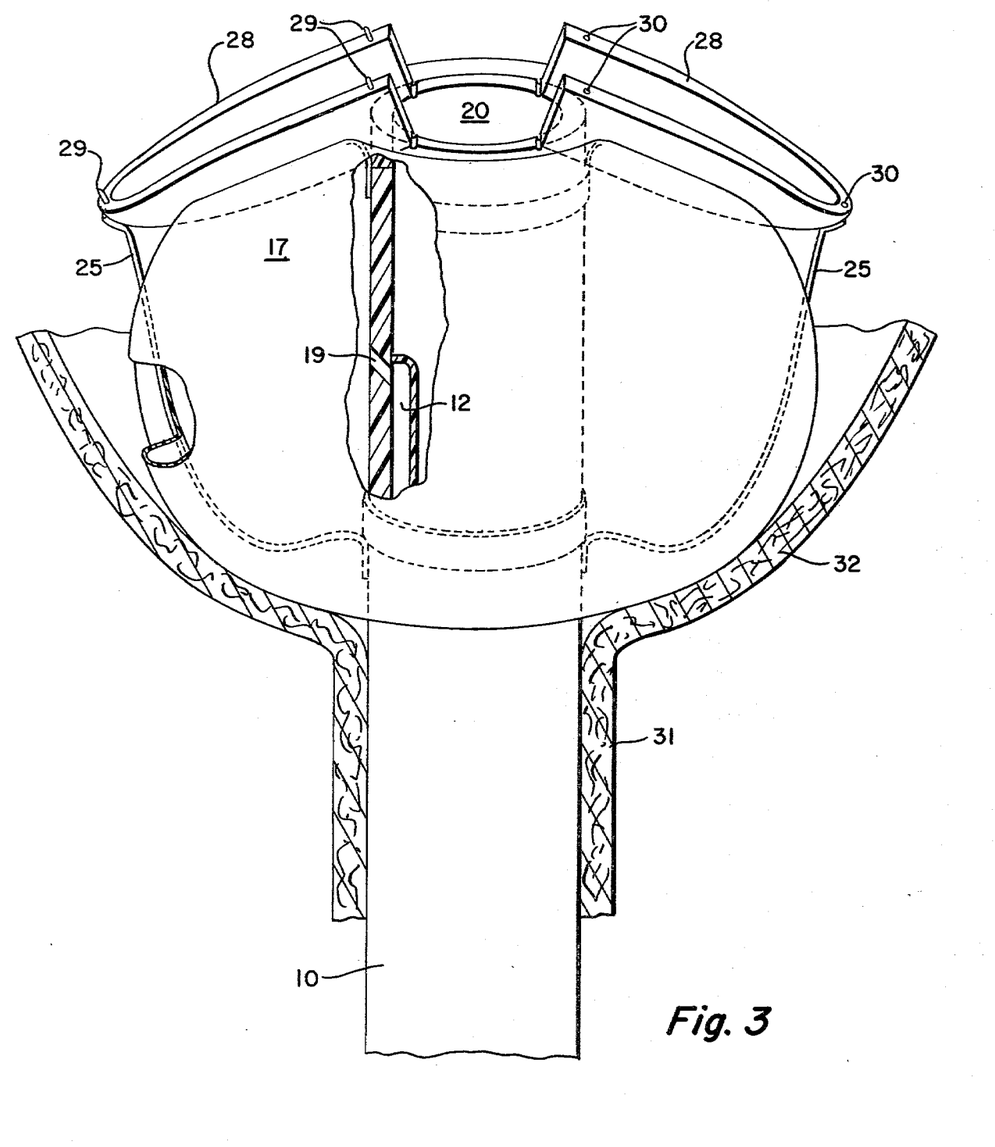
FIG. 3 is an enlarged view of the catheter shown in FIG. 1 but after distention of the retention balloon to expose the drainage lumen within the bladder of a patient.

Returning now to FIG. 1, the embodiment of the present invention in its preferred aspect further includes two string like actuating members 25, each of which is adhered at one end to the tubular body portion 10 at a site which is closely adjacent the inflatable balloon 17 and opposite the tip 18. The string members 25 are attached at diametrically-opposite sides of the tubular body portion to traverse the balloon and extend along the tip 18 to the distal end thereof where each string is adhered to the tip. The string members 25 are made of non-absorbent and low friction material such as nylon. The strings are adhered to the tip at opposite sides of a longitudinal parting line 26 which extends from the distal end of the tip along the tip toward the balloon to a point of intersection with the partial transverse parting line 27. The parting line 27, together with parting line 26, divide the tip into two hinged tip segments 28 that are held together, if desired, along the parting line 26 by interlocking pins 29 and sockets 30 which is best shown in FIG. 3. The relationship between parting line 26, at the distal end, and plug assembly 15, at the proximal end, is used to orientate hinged sliding movement along parting line 26 between tip segments 28 while advanced along the urethra.

The urological catheter of the present invention with the soft, pliable tip having the spirally-shaped grooves 22 or hair-like projections 23 is advanced along the urethra to the point where the tip enters the bladder of a patient. Effective guidance is also provided by relative movement between the tip segments along parting line 26, even when pins 29 and sockets 30 are used, to negotiate the usual bends in the male urethra. The appearance of liquid at the proximal end of the catheter indicates that at least a portion of the drainage eyes has entered the bladder, and that distention of the retention balloon can be safely carried out without causing injury to the urethra. An inflating medium is fed through valve means 16 along inflation lumen 12. The medium is delivered by opening 19 into the area enclosed by the balloon producing distention thereof. As the balloon inflates, the string members 25 which pass along the outer surface thereof are moved outwardly from the body portion of the catheter. This movement of the strings 25 develops a sufficient force to draw the hinged tip segments 28 apart, thus opening up the entire cross-sectional area of the drainage lumen 20 in the tip. Distention of the balloon occurs in a radial direction as well as a longitudinal direction in relation to the tubular body portion such that the string members are embedded within the surface upon inflation to a predetermined inflated state. Differential thickening of the wall of the balloon is one way to assure the development of a sufficient force and embedded relationships. At the same time, the tension members draw the displaced halves of the tip segments into a partially-nested relation with the forwardly enlarged portion of the balloon so that the displaced halves of the tip are nested into the balloon. Since the side walls of the divided tip portion are made of soft, pliable material, the bladder wall can safely contact the side wall edges of the tip without occlusion to the drainage opening 20. The actual site for attachment of the actuating strings is chosen to provide the desired amount of displacement movement according to each embodiment.

In FIG. 3, reference numeral 31 identifies the neck of the urethra at the bladder and reference numeral 32 identifies part of the bladder wall. It will be observed that the balloon, after distention, contacts the bladder wall 32 while the string members 25 are safely embedded within the balloon to prevent contact with the wall of the bladder. The string members are, however, made from material bicompatible with the environment of their use and sufficiently elastic to avoid possible damage to the lining of the bladder.

A further aspect to the present invention, as described above, is shown in FIG. 4 where a detachable catheter segment is used as a prosthesis within the urethra at the neck of the bladder. The distal portion of the catheter is subdivided to form an implantable body segment 10A and a carrier segment 10B. The drainage lumen in the carrier segment 10B is separate and distinct from the inflation lumen extending therealong. The inflation lumen remains after segment 10A is implanted and the carrier segment is withdrawn. The inflation lumen is used to collapse the inflatable balloon and withdraw the implanted body segment along the urethra for removal of the prosthesis. It is, therefore, to be understood that the inflation lumen is defined by a discrete member separable from the carrier segment 10B. Reference numeral 33 identifies such a discrete member defining the inflation lumen which extends to the implantable body segment for communication with opening 19.

The proximal end of the implantable body section is divided longitudinally along line 34 forming arcuate segments 35. The arcuate segments are joined together by interlocking pin and socket connectors 36 and 37, respectively. The carrier section 10B is interlocked with the implantable body section 10A by means such as, for example, pin members projecting from the inside surface of the section 10A into socket connectors in the outside wall surface of the carrier segment. It is to be understood, of course, that other suitable interlocking means may be used without departing from the spirit of the present invention. The arcuate segments 35 are connected at diametrically-opposite sites with an end of actuator strings 37. The strings extend along opposite sides of the implantable body section, traversing the inflatable balloon where they are adhered at their free ends to the body portion at a site adjacent the tip. By this relationship of parts upon distention of the inflatable balloon, the strings 37 are displaced outwardly away from the surface of the implantable body segment at the same time and in a similar manner as strings 25 are displaced. This displacement produces tension on strings 37 sufficient to separate the arcuate segments 35 along the parting line outwardly against the side wall of the urethra. In this way, the implantable section of the catheter is anchored against advancing movement into the bladder by the divided wall portions 35 and against withdrawing movement by the inflated balloon. It will be observed, not only in regard to the embodiment of FIG. 4, but also in regard to the embodiments of FIGS. 1-3, that the extent to which the catheter protrudes into the bladder is reduced by the displacement of the hinged halves of the catheter tip against the inflated surface of the balloon. In the embodiment of the present invention shown in FIG. 4, the catheter is particularly useful in the human male urethra. Distention of the inflatable balloon produces an actuator force to displace the hinged tip segments and at the same time displace the hinged segments for retention to maintain the implantable segment at the desired site in the bladder neck. As the arcuate segments 35 are displaced, the carrier segment 10B is disconnected therefrom and withdrawn from the male urethra so that only the inflation lumen, formed by member 33, extends along the urethra from the body of the patient. Member 32 occupies a much smaller space in the urethra as compared with the usual catheter whereby injury and infection are less likely to occur even after prolonged use of the implanted catheter section. Moreover, an additional advantage arises out of the use of an implantable catheter section because a patient is capable of employing his natural sphincter with the attending capability of voiding when so desired. This eliminates the need for collection bags or the like as heretofore been required for continuous drainage through the use of a catheter.

Figure 4:
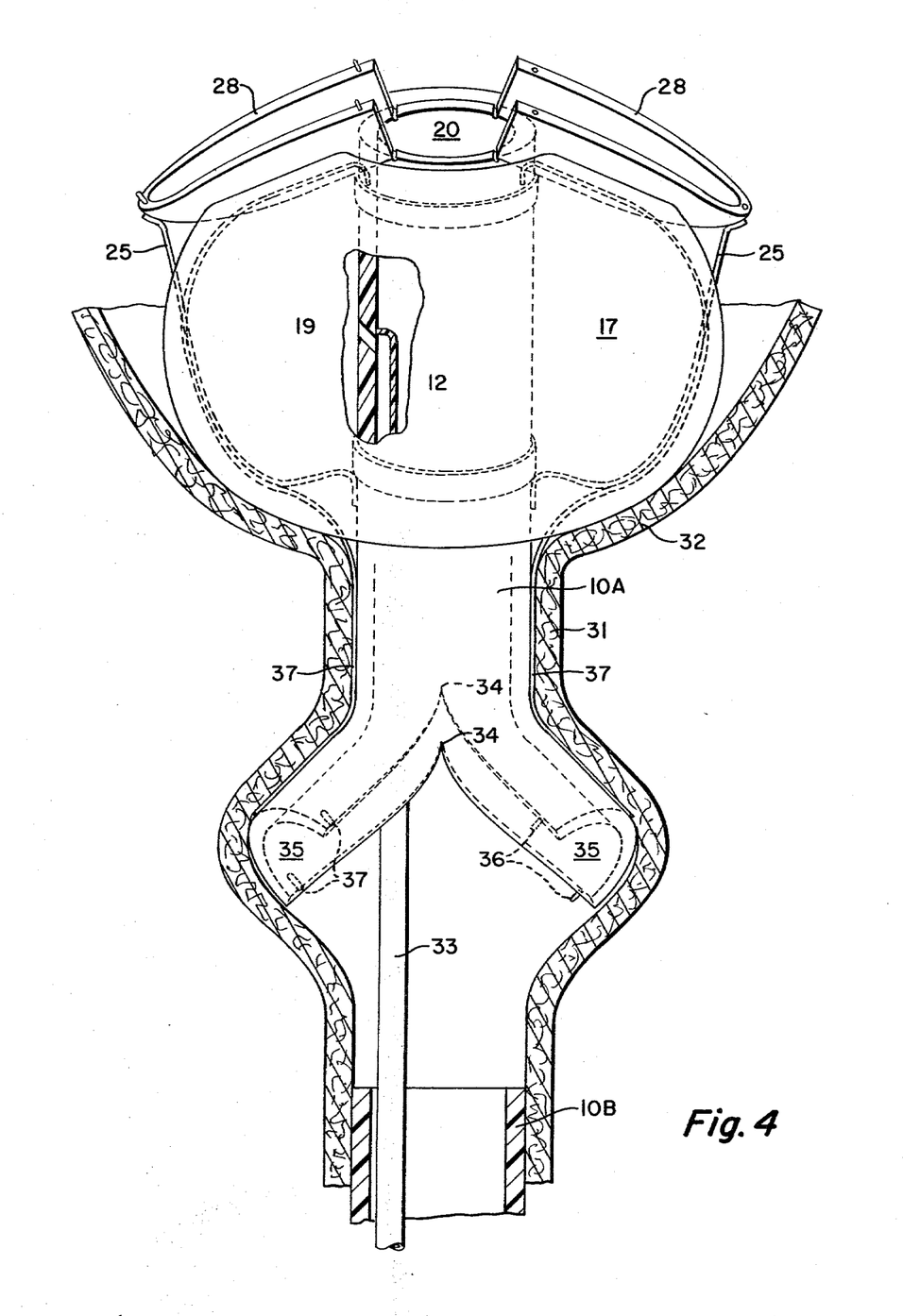
FIG. 4 is a view similar to FIG. 3 but illustrating a further aspect of the present invention wherein a segment of the catheter is retained in the urethra.
Figure 5:
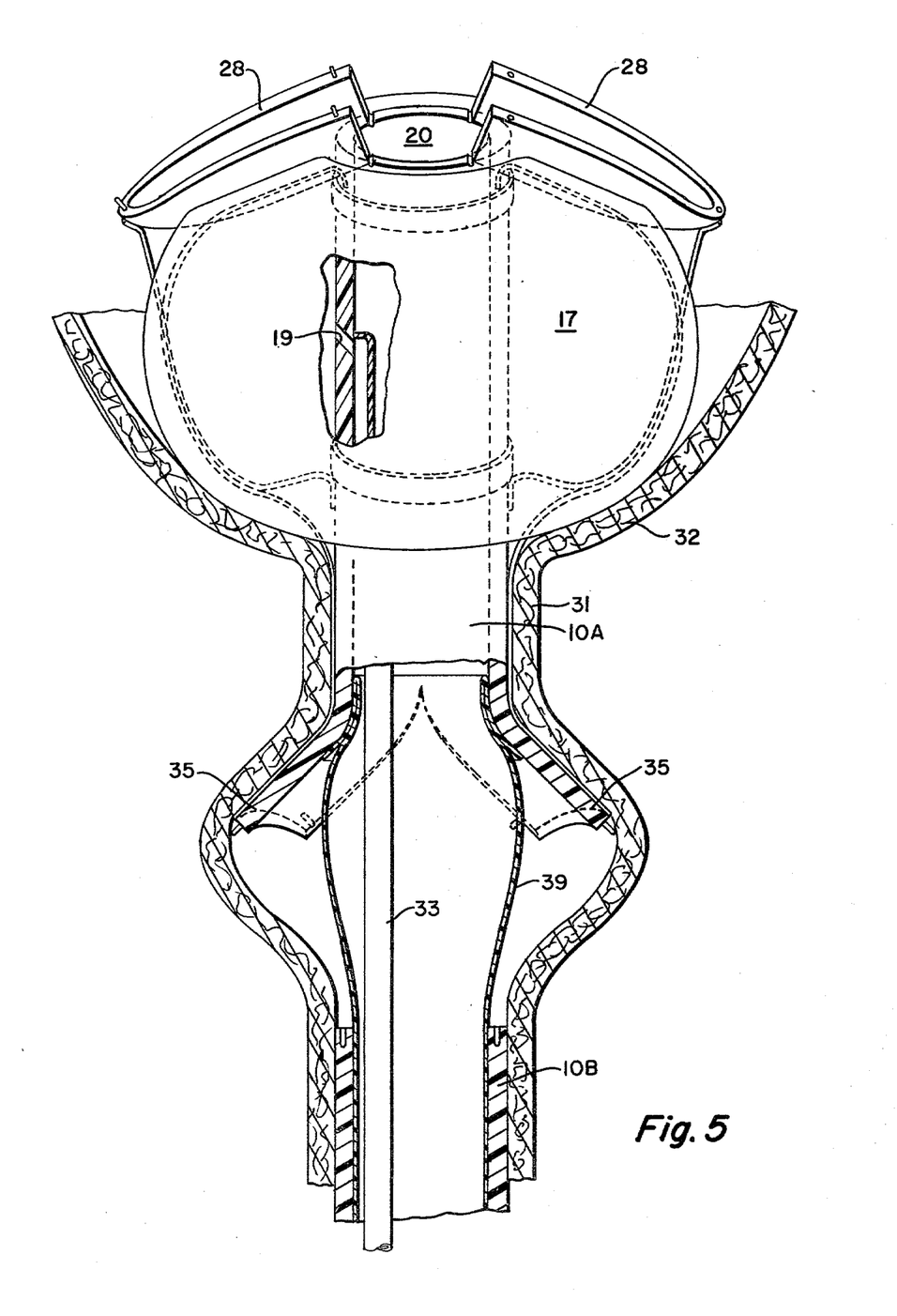
FIG. 5 is a view similar to FIG. 4 but illustrating a further aspect of the present invention wherein a sheathing forms a drainage conduit from an implanted segment of the catheter.

The embodiment of the present invention shown in FIG. 5 differs from that already described in regard to the embodiment of FIG. 4 by the addition of a thin-film of plastic or other material forming a tubular, fluid-conducting conduit 39. The conduit 39 is formed by adhering the thin-film conduit at one end to the inside wall surface of the implantable body section 10A and extending within the carrier section 10B so that after withdrawal of the carrier section 10B from the urethra, a lining is formed in the urethra by the thin-film conduit. It will be observed in regard to the embodiments of FIGS. 3-5 that the distal end of the catheter takes the form of a wineglass shape.

Figure 6:
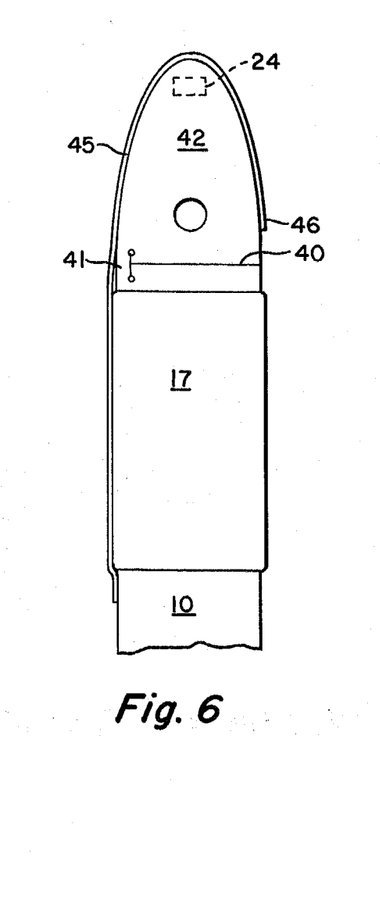
FIG. 6 is a view similar to FIG. 1 but illustrating a further embodiment of the present invention.
Figure 7:
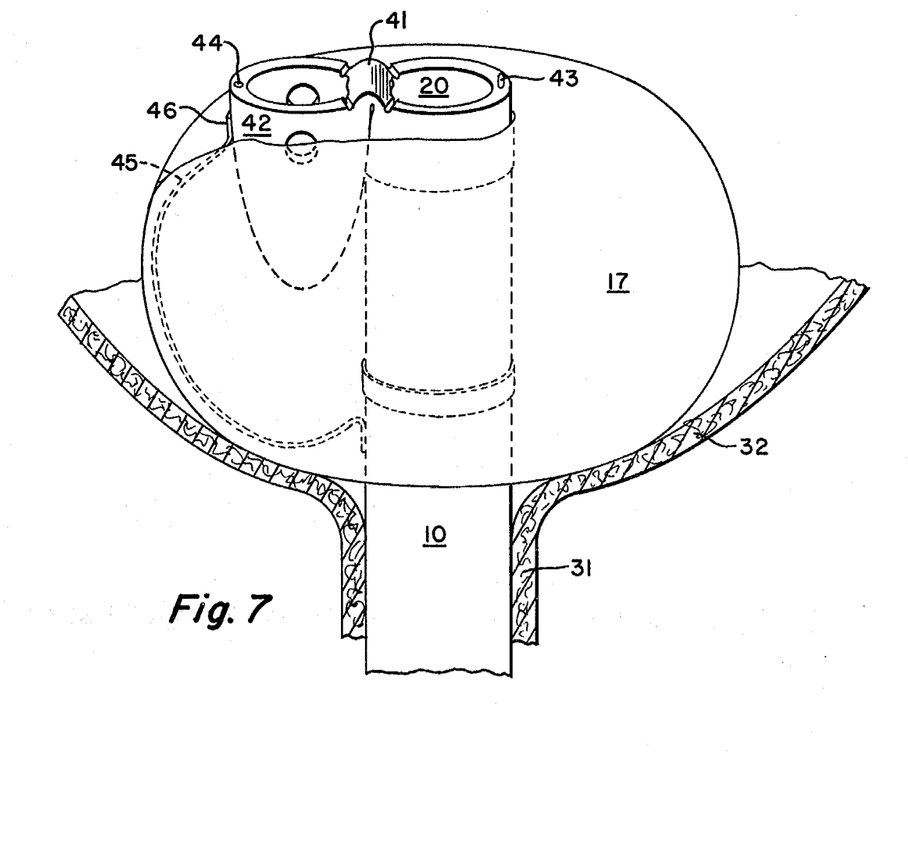
FIG. 7 is a view similar to FIG. 2 but illustrating the relationship of parts upon distention of an inflatable balloon according to the embodiment of FIG. 6.

FIGS. 6 and 7 illustrate an additional embodiment of the present invention which is addressed to a modification to the construction of the catheter tip for the hinged displacement of a tip section. As shown, the tip on the distal end of tubular body portion 10 is partially divided along line 40 which extends transversely to the extended length of the catheter. Line 40 terminates at a hinged wall segment 41 defining thereby a hinged tip section 42. At a site diametrically opposite the hinged wall segment 41, a pin 43 and socket 44 (FIG. 7) are used to form a stabilizing interconnection between the tip section 42 and the remaining portion of the catheter tip. A single string member 45 is attached at one end 46 to the displaceable tip section 42 as shown in FIG. 6 which is closely adjacent the parting line 40. The string is wrapped around the forwardly-directed portion of the cone-shaped tip and extends rearwardly along the catheter traversing the inflatable balloon 17 and adhered at its free end to the tubular body portion 10. Upon entrance of the catheter into the bladder, an inflating medium is introduced into the balloon producing distention thereof with an accompanying displacement of string 45. The displacement of string 45 brings about a hinged movement of the tip 42 from the position shown in FIG. 6 into the position shown in FIG. 7. In the fully-displaced position after the balloon has been inflated to the desired extent, the conical end portion of the tip is moved about 180° from its original position and into a nested position where it extends into the balloon and completely exposes the drainage lumen 20 of the tip. The balloon may be constructed and arranged to inflate at only one side of the catheter instead of circumferentially. The inflated balloon surface must displace the string actuator. If desired, the magnetic insert 24 is embedded within the terminal end wall of the tip. Moreover, another magnet diametrically located in the main body of the catheter will help keep the tip in its nested position. The parting line 40 is smoothed out, grooved or provided with hair-like projections to reduce friction during directional insertion. The valve means 16 indicates direction of flexion of the tip 42 in the same manner as previously described in regard to FIG. 1. This aspect of the present invention is particularly advantageous according to the embodiment of FIGS. 6 and 7. The hinged tip provides directional guidance control during insertion of the catheter by utilizing hinged flexing movements of the tip segment for guiding and following the curved track of the human male urethra. The catheter is orientated about its longitudinal axis so that the hinged wall segment 41 faces toward the shortest curved sections of the urethra. When inside the male urethra, the hinged tip radially flexes toward the hinged side to negotiate the curved section of the urethra. The inflation plug assembly 15 and valve means 16 are used, inter alia, as an indicator of the orientation of the hinged wall segment to an operator.

FIG. 8 illustrates the use of magnetic means to produce propelling movement through attractive or repulsive lines of magnetic force. As described hereinbefore, a magnetoinsert is carried in the tip of the catheter which can, if desired, be constructed from magnetic material. Magnetic means, such as a permanent magnet or an electromagnet, is used externally of the catheter to generate lines of magnetic force which, depending upon the polarity thereof in relation to the insert, produces a repelling or attractive force on the insert 5in the tip of the catheter. FIG. 8 illustrates a toroidally-shaped coil 50 into which the penis 51 of a patient is placed so that the magnetic lines of force are developed by the coil passing through the urethra in a dependent relation upon the polarity of a low voltage current. An ON-OFF and polarity reversing switch 52 controls the flow of current supplied by batteries, for example. During the initial travel of the catheter, the polarity of the magnetic lines of force is chosen to produce an attractive relation with the magnetoinsert of the tip of the catheter and after the catheter has been passed beyond the toroidal coil, the lines of force are reversed by actuating switch 52 so as to produce a pushing-type propelling movement to facilitate advancing movement of the catheter along the remaining portion of the urethra. FIG. 8 also illustrates an electromagnet 53 employed in a somewhat similar manner but freely movable about the body of a patient. The lines of magnetic force developed by the electromagnet 53 are chosen by selecting the desired current flow direction through the winding in the electromagnet for magnetically attracting the magnetoinsert in the catheter during the initial portion of the travel along the urethra. During this period of catheter movement, the electromagnet is placed at opposite sides of the scrotum 54 as shown and if necessary adjacent the bladder by entrance in the anus which position is shown in FIG. 8 by reference numeral 53A. Movement of the electromagnet about the patient's body facilitates guiding and propelled movements of the catheter particularly along a curved path of the urethra in a male patient including the area identified by reference numeral 55 lying in the vicinity of the prostrate.

Although the invention has been shown in connection with certain specific embodiments, it will be readily apparent to those skilled in the art that various changes in form and arrangement of parts may be made to suit requirements without departing from the spirit and scope of the invention.

I claim as my invention:

1. A flexible retention catheter comprising an elongated tubular body portion defining a drainage lumen, an inflatable balloon forming a sheath around said body portion adjacent one end thereof, an inflation lumen disposed in association with said tubular body portion to extend into communication with said balloon for conducting an inflating medium, and a soft, pliable cone-shaped tip at the end of said body portion adjacent said balloon, said tip having a side wall defining a drainage eyelet extending to a drainage lumen terminating at a closed end wall within the tip, said tip having a reduced urethral contact surface defined by recesses for minimizing sliding friction during travel of the tip along the lining of the human urethra.

2. The flexible retention catheter according to claim 1 wherein said urethral contact surface includes spiral grooves extending along said tip from the closed end thereof.

3. The flexible retention catheter according to claim 1 wherein said urethral contact surface includes hair-like projections.

4. The flexible retention catheter according to claim 1 wherein said tip is adhered to said tubular body portion adjacent said balloon.

5. The flexible retention catheter according to claim 1 wherein said tubular body portion is comprised of polyvinylchloride plasticized for flexibility, and wherein said tip is comprised of polyvinylchoride plasticized for pliable softness to distort under advancing movement without damage to the lining of a human urethra.

6. The flexible retention catheter according to claim 1 wherein said tubular body portion includes hair-like projections extending from the outer surface thereof for reducing frictional contact with the lining of a human urethra.

7. The flexible retention catheter according to claim 1 wherein the side wall of said tip is severed along at least one line to define at least one hinged tip segment for hinged movement to guide said tip along the lining of a human urethra.

8. The flexible retention catheter according to claim 1 further comprising means to indicate the direction of hinged movement of said tip segment.

9. The flexible retention catheter according to claim 8 wherein said means includes an inflation valve member at a lateral side of said tubular body portion for communication with said inflation lumen.

10. A flexible retention catheter comprising an elongated tubular body portion defining a drainage lumen, an inflatable balloon forming a sheath around said body portion adjacent one end thereof, an inflation lumen disposed in association with said tubular body portion to extend into communication with said balloon for conducting an inflating medium, a soft, pliable cone-shaped tip on the end of said body portion adjacent said balloon, said tip having a side wall defining a drainage eyelet extending to a drainage lumen with a closed end within the tip, and magnetic means including a magnetoinsert supported by said tubular body portion for propelled movement of said tubular body portion into the body of a patient.

11. The flexible retention catheter according to claim 10 wherein said magnetoinsert is embedded within the wall of said tip.

12. The flexible retention catheter according to claim 10 wherein said magnetoinsert is embedded within the wall of said tip at the closed end of the lumen therein.

13. The flexible retention catheter according to claim 10 wherein said magnetic means further includes means externally of said tubular body portion for establishing a force field for advancing repelling movement by said magnetoinsert to thereby direct and guide said tip along a human urethra.

14. The flexible retention catheter according to claim 10 wherein said magnetic means further includes means externally of said tubular body portion for establishing a force field to magnetically attract said magnetoinsert to thereby pull and guide said tip along a human male urethra.

15. The flexible retention catheter according to claim 10 wherein said magnetic means includes an electromagnet.

16. The flexible retention catheter according to claim 10 wherein said magnetic means includes a toroidal electromagnet.

17. The flexible retention catheter according to claim 10 wherein said magnetoinsert comprises a metal insert.

18. The flexible retention catheter according to claim 10 wherein said magnetoinsert comprises a permanent magnet.

19. A flexible retention catheter comprising an elongated tubular body portion defining a drainage lumen, an inflatable balloon forming a sheath around said body portion adjacent one end thereof, a soft, pliable cone-shaped tip portion at the end of said body portion adjacent said balloon, said tip portion having a closed end with a side wall defining a drainage lumen communicating with the drainage lumen of said tubular body portion, the side wall of said tip portion being severed along at least one line to form a hinged tip segment, at least one tension member traversing said balloon and adhered at one end to said hinged tip segment and adhered to the other end of said body portion at the side of said balloon which is remote to said tip segment, and means forming an inflation lumen disposed in association with said body portion to extend into communication with said balloon for conducting an inflating medium to the balloon whereby inflation of the balloon moves said tensioning member to swing the hinged tip segment of said tip against the inflated surface of the balloon for exposing the drainage lumen in said tip portion.

20. The flexible retention catheter according to claim 19 further including valve means coupled to said means forming an inflation lumen at a side of said body portion for indicating the displacement direction of said hinged tip segment.

21. The flexible retention catheter according to claim 19 wherein said hinged tip segment is disposed for hinged guiding movement during insertion along a human urethra.

22. The flexible retention catheter according to claim 19 wherein said inflatable balloon is constructed and attached to said tubular body portion to extend, upon inflation, toward said tip portion for a deformed nested support of said tip segment.

23. The flexible retention catheter according to claim 19 wherein said tubular body portion includes an implanting segment detachably joined to a withdrawal segment.

24. The flexible retention catheter according to claim 23 wherein said implanting segment includes a segmented length having a side wall severed along at least two lines to form hinged retention segments.

25. The flexible retention catheter according to claim 24 further comprising at least one retention tensioning member traversing said balloon and adhered at one end to one of said hinged retention segments and adhered at the other end to said body portion whereby inflation of said balloon moves said retention tensioning member to swing the hinged retention segment adhered thereto outwardly against the urethral lining for implanted support thereby.

26. The flexible retention catheter according to claim 24 further comprising at least two retention tensioning members traversing said balloon and each adhered at one end to one of said hinged retention segments and adhered at the other end to said body portion whereby inflation of the balloon moves said retention tensioning members to swing the hinged retention segments adhered thereto outwardly against the urethral lining for implanted support thereby.

27. The flexible retention catheter according to claim 23 wherein said implanting segment includes releasable means to hold the severed side walls of said hinged retention segments together.

28. The flexible retention catheter according to claim 23 wherein said means forming an inflation lumen includes a lumen wall discrete from said withdrawal segment.

29. The flexible retention catheter according to claim 28 wherein said lumen wall is adjoined to said implanting segment.

30. The flexible retention catheter according to claim 23 further comprises a collapsible sheath adhered at one end to said implanting segment in a fluid-conducting relation with the drainage lumen thereof.

* * * * *